United States Patent

Tuba et al.

[11] Patent Number: 5,583,228
[45] Date of Patent: Dec. 10, 1996

[54] 17-HALOGENO-4-AZAANDROSTENE DERIVATIVES AND PROCESS FOR THE PREPARATION THEREOF

[75] Inventors: Zoltán Tuba; Judit Horváth; János Széles; Mária Lovas née Marsai; Gábor Balogh, all of Budapest, Hungary

[73] Assignee: Richter Gedeon Vegyeszeti Gyar Rt., Budapest, Hungary

[21] Appl. No.: 564,230

[22] PCT Filed: Jun. 24, 1993

[86] PCT No.: PCT/HU93/00040

§ 371 Date: Dec. 6, 1995

§ 102(e) Date: Dec. 6, 1995

[87] PCT Pub. No.: WO95/00532

PCT Pub. Date: Jan. 5, 1995

[51] Int. Cl.⁶ .................................................. C07D 221/18
[52] U.S. Cl. .................................................. 546/77
[58] Field of Search .................................................. 546/77

[56] References Cited

U.S. PATENT DOCUMENTS 4,377,584  3/1983  Rasmusson et al. .................. 514/284

OTHER PUBLICATIONS

Back, T. G. et al. Journal of the Chemical Society, 1962, part 1, pp. 470–476.
Bartan, D. H. R. et al. Tetrahedron Letters, vol. 24, No. 15, 1983, pp. 1605–1608.
Bartan, D. H. R. et al. Journal of Organic Chemistry, 1989, 54(8), 1904–1910.
Bartan, D. H. R., Bashiardes, G., Fourrey, J–L "An Improved Preparation of Vinyl Iodides", Tetrohedron Letters, vol. 24, No. 15, pp. 1605–1608 (1983).

*Primary Examiner*—C. Warren Ivy
*Assistant Examiner*—Lyman H. Smith
*Attorney, Agent, or Firm*—Herbert Dubno; Jonathan Myers

[57] ABSTRACT

The invention relates to novel 4-azaandrostene intermediates of formula (I),

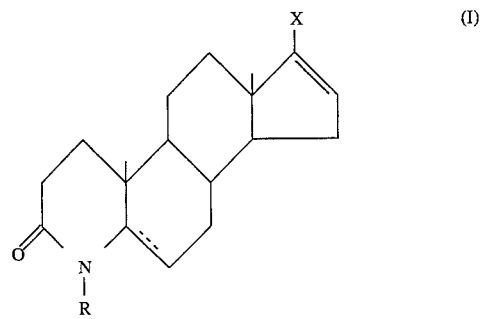

wherein
R is hydrogen or a $C_{1-3}$ alkyl group;
X is chlorine, bromine or iodine; and the
---- bond line is a single or double bond.

9 Claims, No Drawings

17-HALOGENO-4-AZAANDROSTENE DERIVATIVES AND PROCESS FOR THE PREPARATION THEREOF

This is the national type application of PCT/HU93/00040.

This invention relates to 4-azaandrostene derivatives of formula (I)

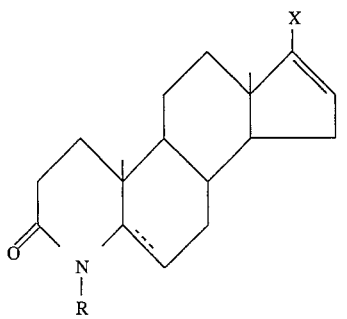

wherein
R is hydrogen or a $C_{1-3}$alkyl group;
X is chlorine, bromine or iodine; and the
---- bond line is a single or double bond.

Furthermore, the invention relates to a process for the preparation of the above compounds.

The compounds of formula (I) can advantageously be used for the preparation of compounds inhibiting the 5α-reductase enzyme. For this synthetic purpose a compound of formula (I) is reacted with a primary or secondary alkylamine preferably in dimethylformamide medium, in a carbon monoxide atmosphere in the presence of palladium(II) acetate, triphenylphosphine and triethylamine and then, if desired, the double bond of the $\Delta^{16}$17β-carboxamido derivative is catalytically hydrogenated. (See Examples 9 and 10.)

The inhibitors of 5α-reductase enzyme impede the transformation of testosterone to dihydrotestosterone and therefore, they can be useful for healing dihydrotestosterone-dependent diseases, e.g. prostatic hyperplasia, acne, seborrhoea and female hirsutism.

BACKGROUND OF THE INVENTION

It is known [J. Chem. Soc. pages 470 to 476 (1962)] that 17-iodo-androsta-5,16-dien-3β-ol is obtained by reacting the 17-hydrazone derivative of dehydroepiandrosterone with elemental iodine in the presence of triethylamine in tetrahydrofuran. By using pregnenolone-20-hydrazone as starting material, under similar reaction conditions 20-iodopregna-5,20-dien-3β-ol can be prepared.

The further development of the above process by investigating the role of base and water is discussed in another literature reference [Tetrahedron Letters 24, pages 1605 to 1608 (1983)]. According to this publication the 17-hydrazone of dehydroepiandrosterone is similarly used as starting material, but tetramethylguanidine is employed as base. The transformation of non-steroid hydrazone derivatives is also exemplified.

The reaction of hydrazone derivatives with N-bromo-or N-chlorosuccinimide is discussed in a publication [Chem. Pharm. Bull. Japan 11, pages 1413 to 1417 (1963)]; according to this the 17-hydrazone derivative of epiandrosterone is used as starting material, which is reacted with N-bromo- or N-chlorosuccinimide. This reaction becomes complete within a few minutes, which can be observed on cessation of the evolution of nitrogen. After pouring onto water the reaction mixture is extracted and then the "vinyl halide-type" compounds formed are purified by chromatography or recrystallization.

A similar method is published also in the Hungarian patent No. 171,166. In this process the hydrazone of androst-2-en-17-one is reacted with an N-halogenosuccinimide in pyridine at a temperature between −30° C. and +20° C. to obtain the "vinyl halide-type" final product.

SUMMARY OF THE INVENTION

According to our invention the preparation of the compounds of formula (I) comprises a) reacting a compound of formula (II)

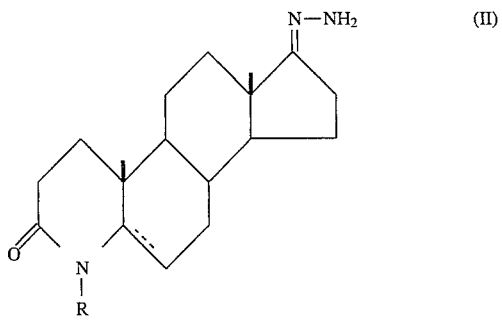

wherein R and the ---- bond line are as defined above, with elemental iodine in the presence of a tertiary amine base in a halogenated hydrocarbon or an aromatic hydrocarbon solvent or in a mixture thereof, or in an ether-type solvent
to obtain compounds of formula (I) containing iodine as X; or b) reacting a compound of formula (II), wherein R and the ---- bond line are as defined above, with N-chloro- or N-bromosuccinimide, respectively in pyridine optionally substituted by one or more $C_{1-4}$alkyl group(s) as solvent at a temperature between −10° C. and +10° C. to obtain compounds of formula (I) containing chlorine or bromine as X.

According to the above process a) the iodination is preferably carried out at room temperature. After completion of the reaction (indicated by cessation of the nitrogen gas evolution), the tertiary amine base and the excess of iodine are removed by treatment with dilute aqueous hydrochloric acid and then with sodium thiosulfate. Subsequently, the solvent is distilled off and the crude product obtained is purified by chromatography and recrystallization. The iodination reaction is preferably carried out in a halogenated or an aromatic hydrocarbon solvent, preferably in chloroform, benzene or a mixture of these solvents or an ether-type solvent, preferably tetrahydrofuran in the presence of a tertiary amine base, preferably triethylamine or tetramethylguanidine at room temperature.

According to the above process b) compounds of formula (I) containing chlorine or bromine, respectively as X are preferably prepared by dissolving a compound of formula (II) in pyridine and then portionwise adding N-chloro- or N-bromosuccinimide, respectively to the above solution at a temperature between −10° C. and +10° C. After complete reaction indicated by cessation of the nitrogen gas evolution the crude product is precipitated by adding water, filtered, washed with water until it becomes free from pyridine, dried and purified by chromatography and subsequent recrystallization. The halogenation with N-chloro- or N-bromosuccinimide, respectively is preferably performed at 0° C. temperature.

The 17-hydrazone derivatives of formula (II) used as starting material in the process according to the invention are prepared as follows.

After dissolving 4-aza-5α-androstane-3,17-dione, 4-azaandrost-5-ene-3,17-dione or 4-methyl-4-aza-5α-androstane-3,17-dione, respectively [known from the literature references: J. Pharm. Sci. 63, pages 19 to 23 (1974); J. Med. Chem. 27, page 1690 (1984); J. Org. Chem. 46, pages 1442 to 1446 (1981)] in alcohol, then triethylamine and hydrazine hydrate are added to the solution and the obtained reaction mixture is boiled under reflux. After completion of the reaction the excess of hydrazine hydrate and triethylamine is distilled off (by evaporating the reaction mixture to about one tenth of its original volume). The residue is precipitated by adding water and after filtering the precipitate is washed with water until neutral and dried. The crude product obtained can be used for the preparation of compounds of formula (I) without any purification.

The invention is illustrated in detail by the following non-limiting Examples.

EXAMPLE 1

Preparation of 17-hydrazono-4-aza-5α-androstan-3-one

To a suspension containing 10 g (0.0346 mol) of 4-aza-5α-androstane-3,17-dione in 100 ml of ethanol 14 ml (0.1 mol) of triethylamine and 50 ml (1.0 mol) of hydrazine hydrate are added and the mixture is boiled under reflux for 3 hours. (The progress of the reaction is followed by thin layer chromatography.) After the reaction has become complete the reaction mixture is cooled down, the solution is evaporated to one tenth of its original volume and the product is precipitated by adding about a 10-fold volume of water. After compaction the precipitate is filtered, washed with water until neutral and dried to obtain the title compound.

Yield: 9.44 g (90%), m.p.: 254°–258° C.

$^1$H-NMR (300 MHz, CDCl$_3$) δppm: 0.86 (s,3H,18-CH3), 0.93 (s,3H,19-CH$_3$), 2.41 (m,2H,H-2), 3.07 (dd,1H,H-5), 4.77 (br,2H,NH$_2$), 5.74 (br,1H,NH).

EXAMPLE 2

Preparation of 17-hydrazono-4-azaandrost-5-en-3-one

The process described in Example 1 is followed, except that 4-azaandrost-5-ene-3,17-dione is used as starting substance to obtain the title compound.

Yield: 35%, m.p.: 379°–382° C.

IR (KBr) v: 1633 (C=C), 1661 (C=N), 1693 (C=O), 3200 (NH), 3350 (NH$_2$) cm$^{-1}$.

EXAMPLE 3

Preparation of 17-hydrazono-4-methyl-4-aza-5α-androstan-3-one

The process described in Example 1 is followed, except that 4-methyl-4-aza-5α-androstane-3,17-dione is used as starting substance to give the title compound.

Yield: 75%, m.p.: 211°–218° C.

$^1$H-NMR (300 MHz, CDCl$_3$) δppm: 0.86 (s,3H,18-CH$_3$), 0.91 (s,3H,19-CH$_3$), 2.93 (s,3H,N—CH$_3$), 3.05 [dd(J=3.6; J=12.6), 1H, H-5], 4.78 (v br, 2H,NH$_2$).

EXAMPLE 4

Preparation of 17-iodo-4-aza-5α-androst-16-en-3-one

After dissolving 9.1 g (0.03 mol) of 17-hydrazono-4-aza-5α-androstan-3-one in 1200 ml of an 1:1 chloroform/benzene mixture and adding 90 ml of triethylamine, 11.4 g (0.045 mol) of iodine dissolved in 110 ml of benzene are dropwise added to the above solution. The reaction mixture is stirred at room temperature for an additional 60–90 minutes. (The progress of the reaction is followed by thin layer chromatography). After complete occurrence of the reaction the obtained solution is diluted with 500 ml of chloroform and successively washed with 10% aqueous hydrochloric acid solution, water, 5% aqueous sodium thiosulfate solution, water, 5% aqueous sodium hydrogen carbonate solution, finally with water and dried over anhydrous sodium sulfate. After evaporating the solvent under reduced pressure the residue is purified by chromatography on a silica gel column by using first chloroform and subsequently a 95:5 chloroform/acetone mixture as eluents. The product obtained is recrystallized from ethanol to give the title compound.

Yield: 5.9 g (50%), m.p.: 278°–282° C.

$^1$H-NMR (300 MHz, CDCl$_3$) δppm: 0.73 (s,3H,18-CH$_3$), 0.91 (s,3H,19-CH$_3$), 3.1 (dd,1H,H-5), 6.18 (m, 1H,H-16), 6.9 (br, 1H, NH).

By using an identical amount of tetramethylguanidine instead of triethylamine in the above reaction, the title compound is obtained in a yield of 65% with the same physical characteristics as given above.

EXAMPLE 5

Preparation of 17-iodo-4-azaandrosta-5,16-dien-3-one

The process described in Example 4 is followed, except that 17-hydrazono-4-azaandrost-5-en-3-one is used as starting substance to obtain the title compound. Yield: 57%, m.p.: 227°–230° C.

$^1$H-NMR (300 MHz, CDCl$_3$) δppm: 0.78 (s,3H,18-CH$_3$), 1.13 (s,3H,19-CH$_3$), 4.9 [dd(J=2.4; J=5.1) ,1H,H-6], 6.15 [dd(J=3.2; J=1.7),1H,H-16], 8.27 (br,1H,NH).

EXAMPLE 6

Preparation of 17-iodo-4-methyl-4-aza-5α-androst-16-en-3-one

The process described in Example 4 is followed, except that 17-hydrazono-4-methyl-4-aza-5α-androstan-3-one is used as starting substance and the reaction is carried out in benzene. The title compound is obtained in a yield of 52%, m.p.: 176°–181° C.

$^1$H-NMR (300 MHz, CDCl$_3$) δppm: 0.74 (s,3H,18-CH$_3$), 0.92 (s,3H,19-CH$_3$), 2.94 (s,3H,N-CH$_3$), 3.07 [dd(J=3.7; J=12.6), 1H, H-5], 6.13 [dd(J=3.2; J=1.7),1H,H-16].

EXAMPLE 7

Preparation of 17-chloro-4-methyl-4-aza-5α-androst-16-en-3-one

A solution containing 4 g (0.0126 mol) of 17-hydrazono-4-methyl-4-aza-5α-androstan-3-one in 40 ml of anhydrous pyridine is cooled to 0° C. and the solution of 3.2 g (0.024 mol) of N-chlorosuccinimide in 40 ml of pyridine is dropwise added under vigorous stirring. After cessation of the violent nitrogen gas evolution the reaction mixture is stirred for an additional 15 minutes and then dropped to 800 ml of water. After compaction of the precipitate the crude product is filtered, washed with water until neutral and dried over phosphorus pentoxide under reduced pressure at room temperature. The crude product obtained is purified by chromatography on a silica gel column by using chloroform as eluent. After recrystallization of the evaporation residue from petroleum ether the title compound is obtained in a yield of 2.15 g (53%), m.p.: 139°–140° C.

$^1$H-NMR (300 MHz, CDCl$_3$) δppm: 0.88 (s,3H,18-CH$_3$), 0.93 (s,3H,19-CH$_3$), 2.89 (s,3H,N-CH$_3$), 3.0 (dd, 1H,H-5), 5.53 (m, 1H,H-16).

EXAMPLE 8

Preparation of 17-bromo-4-methyl-4-aza-5α-androst-16-en-3-one

The process described in Example 7 is followed by using 17-hydrazono-4-methyl-4-aza-5α-androstan-3-one as starting substance and N-bromosuccinimide as reactant to give the title compound. Yield: 55%, m.p.: 159°–161° C.

$^1$H-NMR (300 MHz, CDCl$_3$) δppm: 0.82 (s,3H,18-CH$_3$), 0.91 (s,3H,19-CH$_3$), 2.86 (s,3H,N-CH$_3$), 3.0 (dd,1H,H-5), 5.68 (m,1H,H-16).

EXAMPLE 9

Preparation of 3-oxo-4-aza-5α-androst-16-ene-17β-(N-tert-butylcarboxamide)

To a solution containing 3.99 g (0.01 mol) of 17-iodo-4-aza-5α-androst-16-en-3-one in 150 ml of dimethylformamide, 0.224 g (0.001 mol) of palladium(II) acetate, 0.524 g (0.002 mol) of triphenylphosphine, 10 ml of triethylamine and 15 ml (0.14 mol) of tertiary butylamine are added and the mixture is heated at 60° C. under carbon monoxide for 90 to 120 minutes. (The progress of the reaction is followed by thin layer and gas chromatography.) After the reaction has become complete the amines and dimethylformamide are distilled off under reduced pressure, then the residue is dissolved in 150 ml of chloroform and successively washed with water, 5% aqueous hydrochloric acid solution, saturated aqueous sodium hydrogen carbonate solution and saturated aqueous sodium chloride solution until neutral and finally dried over anhydrous sodium sulfate. After evaporating the solvent the residue is purified by chromatography on a silica gel column by using ethyl acetate as eluent to obtain the title compound. Yield: 3.16 g (85%), m.p.: 292°–297° C.

$^1$H-NMR (300 MHz, CDCl$_3$) δppm: 0.93 (s,3H,19-CH$_3$), 1.0 (s,3H,18-CH$_3$), 1.4 (s,3H,C(CH$_3$)$_3$), 2.15 (m,2H,H-15a+ H-15b), 2.4 (m,2H,H-2), 3.08 [dd (J=4.5; J=7.0),1H,H-5], 5.48 (br s,1H,NH), 5.6 (br s,1H,NH), 6.18 [dd (J=1.7; J=1.4),1H,H-16].

EXAMPLE 10

Preparation of 3-oxo-4-aza-5α-androstane-17β-(N-tert-butylcarboxamide)

A suspension containing 1 g of palladium-on-carbon catalyst in 6 ml of water is added to a solution containing 1 g of 3-oxo-4-aza-5α-androst-16-ene-17β-(N-tert-butylcarboxamide) in 40 ml of formic acid under nitrogen. The heterogeneous mixture is stirred at room temperature for 4 to 5 hours. The progress of the reduction is followed by thin layer chromatography. After the reaction has become complete the catalyst is filtered off and washed with an 1:1 mixture of chloroform/methanol. After evaporation of the combined solution to dryness, the residue is triturated with water, the precipitate is filtered and washed with water to give the title compound Yield: 90%, m.p.: 283°–286° C.

We claim:
1. A compound of the formula (I),

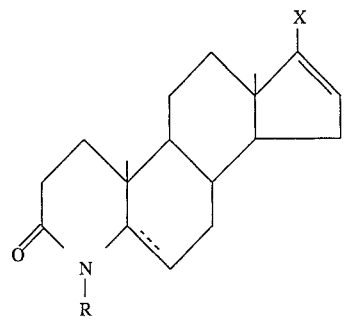

wherein

R is hydrogen or a C$_{1-3}$alkyl group;

X is chlorine, bromine or iodine; and the

---- bond line is a single or double bond.

2. A compound of the formula (I) defined in claim 1 and selected from the group consisting of 17-iodo-4-aza-5α-androst-16-en-3-one, 17-iodo-4-aza-androsta-5,16-dien-3-one, 17-iodo-4-methyl-4-aza-5α-androst-16-en-3-one, 17-chloro-4-methyl-4-aza-5α-androst-16-en-3-one and 17-bromo-4-methyl-4-aza-5α-androst-16-en-3-one.

3. A process for the preparation of a compound of the formula (I),

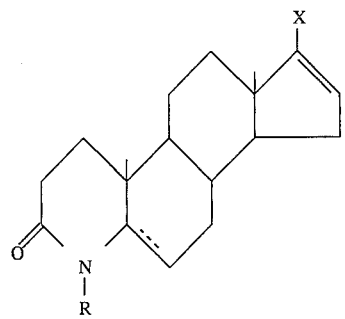

wherein

R is hydrogen or a C$_{1-3}$alkyl group;

X is chlorine, bromine or iodine; and the

---- bond line is a single or double bond, which comprises a) reacting a compound of the formula (II)

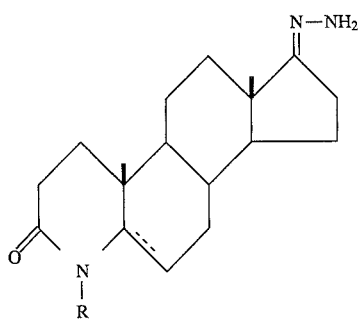

, with elemental iodine in the presence of a tertiary amine base in a halogenated hydrocarbon or benzene solvent or in a mixture thereof, to obtain a compound of the formula (I) containing iodine as X; or b) reacting a compound of the formula (II), with N-chloro- or N-bromosuccinimide, respectively in pyridine optionally substituted by at least one $C_{1-4}$alkyl group as solvent at a temperature between $-10°$ C. and $+10°$ C.

to obtain a compound of the formula (I) containing chlorine or bromine as X.

4. A process as claimed in process a) of claim 3, which comprises using chloroform as a halogenated hydrocarbon solvent.

5. A process as claimed in process a) of claim 3, which comprises using triethylamine or tetramethylguanidine as a tertiary amine base.

6. A process as claimed in process b) of claim 3, which comprises using pyridine as solvent.

7. A process as claimed in process b) of claim 3, which comprises carrying out the reaction at 0° C.

8. A process as claimed in process a) of claim 3 for the preparation of 17-iodo-4-aza-5α-androst-16-en-3-one, 17-iodo-4-azaandrosta-5,16-dien-3-one or 17-iodo-4-methyl-4-aza-5α-androst-16-en-3-one, of the formula (I) wherein 17-hydrazono-4-aza-5α-androstan-3-one, 17-hydrazono-4-azaandrost-5-en-3-one or 17-hydrazono-4-methyl-4-aza-5α-androstan-3-one, respectively is the starting material of the Formula (II).

9. A process as claimed in process b) of claim 3 for the preparation of 17-chloro-4-methyl-4-aza-5α-androst-16-en-3-one or 17-bromo-4-methyl-4-aza-5α-androst-16-en-3-one, of the formula (I) wherein 17-hydrazono-4-methyl-4-aza-5α-androstan-3-one is the starting material of the formula (II).

* * * * *